(12) United States Patent
Rao et al.

(10) Patent No.: US 7,081,260 B2
(45) Date of Patent: Jul. 25, 2006

(54) α-GLUCOSIDASE INHIBITORS FROM A NATURAL SOURCE

(75) Inventors: Janaswamy Madhusudana Rao, Hyderabad (IN); Pullela Venkata Srinivas, Hyderabad (IN); Vummenthala Anuradha, Hyderabad (IN); Ashok Kumar Tiwari, Hyderabad (IN); Amtul Zehra Ali, Hyderabad (IN); Jhillu Singh Yadav, Hyderabad (IN); Kondapuram Vijaya Raghavan, Hyderabad (IN)

(73) Assignee: Council of Scientific and Industrial Research, New Dehli (IN)

( * ) Notice: Subject to any disclaimer, the term of this patent is extended or adjusted under 35 U.S.C. 154(b) by 176 days.

(21) Appl. No.: 10/282,011

(22) Filed: Oct. 29, 2002

(65) Prior Publication Data

US 2004/0081711 A1   Apr. 29, 2004

(51) Int. Cl.
*A01N 65/00* (2006.01)

(52) U.S. Cl. ...................... 424/734; 514/866
(58) Field of Classification Search ................ 424/734; 514/866, 894; 549/435; 548/540
See application file for complete search history.

(56) References Cited

U.S. PATENT DOCUMENTS 6,358,998 B1 * 3/2002 Sugano et al. .............. 514/469

FOREIGN PATENT DOCUMENTS

| EP | 000488513 A2 | * | 10/1991 |
| JP | 05043458 A | * | 2/1993 |
| JP | 11246427 A | * | 9/1999 |
| JP | 2001151676 A | * | 6/2001 |

OTHER PUBLICATIONS

Loder et al. Australian Journal of Chemistry (1969), 22(7), 1531-8. Tumor inhibitory plants; amides of Piper novae-hollandiae.*
The Merck Manual of Medical Information: Home Edition (1999), Simon & Schuster, Ince (USA), pp. 748-749.*
Ye, F. et al. Phytomedicine (Mar. 2002), 9(2): 161-166. Alpha-glucosidase inhibitions from a Chinese medical herb (Ramulus mori) in normal and diabetic rats and mice. Abstract.*
Banerji et al., Indian J. Chem., vol. 17B, pp. 538 (1979).
Dasgupta et al., Indian J. Chem., vol. 17B, pp. 538-540 (1979).
Su et al., J. Agric. Food Chem., vol. 29, pp. 115-118 (1981).
Banerji et al., Phytochemistry, vol. 28, No. 11, pp. 3039-3042 (1989).
Jacobson, Notes, vol. 71, pp. 366-367 (1949).
Gupta et al., Phytochemistry, vol. 15, pp. 425 (1976).
Bowden et al., "The Local Anaesthetic in Pagara xanthoxyloides," pp. 3503-3505(1963).
Dutta et al., Indian J. Chem., vol. 14B, pp. 389-390 (1976).
Dhar et al., Indian J. Chem., vol. 5, pp. 588-589 (1967).
Banerji et al., Indian Journal of Chemistry, vol. 19B, pp. 346-349 (1980).
Jensen et al., Phytochemistry, vol. 33, No. 3, pp. 523-530 (1993).
Malhotra et al., Phytochemistry, vol. 29, No. 8, pp. 2733-2734 (1990).
Koul et al. Phytochemistry, vol. 27, No. 11, pp. 3523-3527 (1988).
Gupta et al., Phytochemistry, vol. 11, pp. 2646 (1972).
Banerji et al., Phytochemistry, vol. 13, pp. 2327-2328 (1974).
Banerji et al., "Amides of *Piper retrofractum*", pp. 279-284 (1984).
Kubo et al., Experientia, vol. 40, pp. 340-341 (1984).

(Continued)

*Primary Examiner*—Michele Flood
(74) *Attorney, Agent, or Firm*—Birch, Stewart, Kolasch & Birch, LLP

(57) ABSTRACT

The present invention relates to a method for providing α-glucosidase inhibition to a subject by administering a pharmaceutical composition comprising a α-glucosidase inhibitory agent selected from pipataline (formula 1a), sesamin (formula 1b), pellitorine (Formula 1c), guineensine (Formula 1d) and brachystamide-B (formula 1e) having therapeutic application for diabetes mellitus, cancer, viral diseases such as hepatitis B and C, HIV, AIDS etc; also the invention provides a process for the isolation of said α-glucosidase inhibitory agent from the plant source *Piper longum* in significant yields.

2 Claims, 2 Drawing Sheets

OTHER PUBLICATIONS

Kiuchi et al., Chem. Pharm. Bull., vol. 36, No. 7, pp. 2452-2465 (1988).

Likhitwitayawuid et al., Tetrahedron, vol. 43, No. 16, pp. 3689-3694 (1987).

Ginesta et al., Biosci. Biotech. Biochem., vol. 58, No. 5, pp. 936-937 (1994).

Tabuneng et al., Chem. Pharm. Bull., vol. 31, No. 10, pp. 3562-3565 (1983).

* cited by examiner

Figure 1a
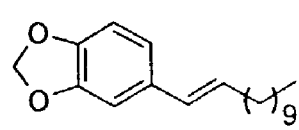
Figure 1b
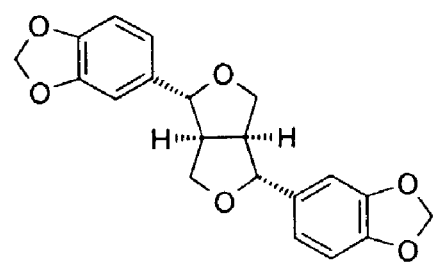
Figure 1c
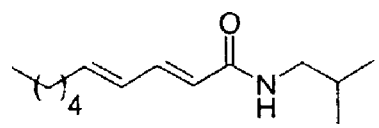
Figure 1d
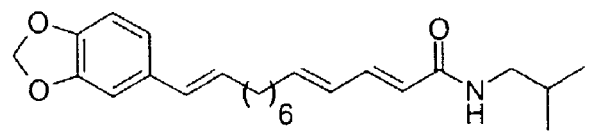
Figure 1e
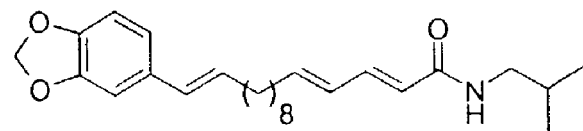
FIGURE 1

Fig 2(a): Graphical representation of α-glucosidase inhibitory pattern of pipataline, sesamine, pellitorine, guineensine and brachystamide-B.

α-GLUCOSIDASE INHIBITORS FROM A NATURAL SOURCE

FIELD OF THE INVENTION

This invention relates to a method for providing α-glucosidase inhibition to a subject by administering a pharmaceutical composition comprising a α-glucosidase inhibitory agent selected from pipataline (formula 1a), sesamin (formula 1b), pellitorine (Formula 1c), guineensine (Formula 1d) and brachystamide-B (formula 1e). In particular this invention relates to the isolation of five compounds namely, pipataline [5-(1-dodecenyl)-1,3-benzodioxol], sesamin [5,5-(tetrahydro-1H,3H-furo(3,4-e)furan-1,4-diyl)bis-1,3-benzodioxol], pellitorine [N-(2-methyl propyl)-2,4-decadienamide], guineensine [13-(1,3-benzodioxol-5-yl)-N(2-methylpropyl)-2,4,12-tri decatrienamide] and brachystamide-B [[15-(1,3-benzodioxol-5-yl)-N(2-methyl-propyl)-2,4,14-pentadecatrienamide] from the plant source *Piper longum* in significant yields. This invention also identifies the therapeutic application of these compounds as α-glucosidase inhibitors in the form of suitable pharmaceutical composition for diabetes mellitus, cancer, viral diseases such as hepatitis B and C, HIV, AIDS etc.

DESCRIPTION OF THE PRIOR ART

The use of plants as medicines goes back to early man. Certainly the great civilization of the ancient Indians, Chinese and North Africans provided written evidences of man's ingenuity in utilizing plants for the treatment of a wide variety of diseases (Phillipson J. D *Phytochemistry*, 2001, 56, 237–243). As new research and clinical experience is broadening the knowledge, changes in drug therapy are also being observed. Due to the occurrence of new diseases and identification of targets with multiple therapeutic applications there is an ongoing search for new compounds having unique structures and properties.

The α-glucosidase enzyme has been identified as such a target. Inhibitors of α-glucosidase are increasingly finding therapeutic application in metabolic disorders such as diabetes mellitus, obesity, hyperlipoproteinemia Type IV (Trusch E., et al., *Angew. Chem. Int. Ed. Engl.* 1981,20, 744–761; Puls, W. Keupu *Diabetologia*, 1973, 9, 97; Puls, W Habilitationssoh Chrift universitat Dusseldorf 1980), HIV, human hepatitis B virus, human cytomegalovirus and influenza (Heightman T. D. and Vasella A. T., *Angew. Chem. Int. Ed. Engi.* 1999, 38, 750–770; Mehta et al., FEBS Lett. 1998,430, 17–22; Watson A. A. et al., *Phytochemistry* 2001, 56, 265–295), cancer and in immuno-compromised cases. The serum level of glucosidases have been found to be increased in many patients with different tumors (Woollen, J. W. and Tesiar, P. 1965, *'din. Chem. Ada.* 12, 671–683) and are being realized to be involved in the degradation of the extracellular matrix and in tumor cell invasion (Bemaki, R. J. et al., 1985 *Cancer Metastasis Rev* 4, 81–102). Therefore, inhibitors of catabolic glucosidases are being actively pursued as a therapeutic strategy for cancer (Watson, A. A. et al., *Phytochemistry* 2001, 56, 265–295).

A variety of compounds having α-glucosidase inhibiting potential have been reviewed for their chemotherapeutic values (E1 Ashry et al., *Pharmazie*, 2000, 55, 251–262, 331–348 and 403–415). Although several drugs targeted for α-glucosidase inhibition are either in clinical use or various stages of clinical development (Drugs of the Future 1986, 11, 795–797; Drugs of the future 1986, 11, 1039–1042; Watson A. A. et al., *Phytochemistry* 2001, 56, 265–295) the impact of the burden of diseases as discussed above underscores the clear need for new agents. It is also necessary to have a large pool of inhibitors as patients can develop resistance to current regimens.

Historically, the knowledge gained from traditional medicinal practice and the screening of the extracts from plants and animals has yielded novel natural products which themselves are potential bioactive agents for the treatment of human diseases (Gullo. V.P., The discovery of natural products with therapeutic potential, Butterworth-Heinemann, Boston, 1994; Cragg G. *Metal J. Nat. Prod.* 1997, 60: 52–60).

The screening of natural sources has led to the discovery of many clinically useful drugs that play a major role not only in the treatment of diseases discussed above, but also in the prevention of such diseases. Therefore, increasing clinical importance of epidemics of diabetes, cancer, HIV and other viral diseases as well as drug resistance has led additional urgency to identify novel resources to provide a large pool of active compounds.

As described hereafter, our search for α-glucosidase inhibitors from traditional medicinal plants has led to the identification of *Piper longum* which contained in significant yield potent α-glucosidase inhibitors.

*Piper longum* Linn. (Pippali) has been described in traditional medical practice of India for malarial fever, heart disease, splenomegaly, cough, edema and so on (P.V.Sharma, Classical uses of medicinal plants, Haridas Ayurveda series (4), Chaukambha Viswabharathi, Varanasi, 1996)

The present invention relates to the identification and isolation of potent α-glucosidase inhibitors from *Piper longum* in the form of suitable pharmaceutical compositions which may find therapeutic application in the treatment of diabetes mellitus, cancer, tumor, metastasis, immunomodulation and as broad spectrum antiviral agents.

Various *Piper* species from which compounds claimed in this invention as α-glucosidase inhibitors have been obtained are tabulated in table 1 and their biological activities are shown in table 2.

Application and Administration:

The α-glucosidase inhibitors of this invention can be applied or administered by any method conventional to the management and treatment of diabetes mellitus, cancer, HIV, AIDS, hepatitis B or hepatitis C, other viral infections, immunocompromised cases, multiple sclerosis, arthritis etc. where o-glucosidase inhibition improves and cures the disease.

For human, animals and/or veterinary application compounds as α-glucosidase inhibitors of the invention may be administered through various routes as per the suitability and clinical condition. For human application compounds as α-glucosidase inhibitors may be administered through various routes including oral, intraperitoneal, intravenous, and/or intramuscular as the case may be.

Formulations:

The compounds as α-glucosidase inhibitors of this invention may be formulated with any pharmaceutically applicable additive, carrier vehicle that by no means should alter the potency and property of the compound in anyway.

For human applications, the compounds of this invention as α-glucosidase inhibitors may be formulated with many of the pharmaceutically acceptable carriers and additives useful for administration of a pharmaceutical compound, which are well known in the art.

The selected carriers or vehicles would of course be consistent with the mode of application or administration of glucosidase inhibitors.

Effective Levels:

The expressions "an effective amount" and or "a suppressive amount" are used to describe that quantity of the α-glucosidase inhibitor compound of the invention which appears necessary to obtain a reduction in the level of disease, such as reduction in post prandial blood glucose level and insulin level in cases of diabetes and suppression of cancer, tumor or viral infection significantly as the case may be, relative to that occurring in an untreated control under suitable conditions of the treatment as per the disease condition and severity. It implies that an effective amount of α-glucosidase inhibitor compound of this invention would be less than any amount that would induce significant unwanted side effects in the organism being treated for a particular disease. This implication is reinforced by the use of the expression "pharmaceutically effective amount". The actual rate and amount of application may vary depending on the disease conditions. This may be irrespective of the concentrations as described in the examples of the invention.

The actual rate and amount of application may vary depending upon the disease and/or infection severity and may also depend upon the plurality of the factors like age and sex of the individual being treated and the mode of administration etc. Upon taking these factors into account, actual dose level and regimen could be readily determined by the person of ordinary skill in the art.

TABLE 1

| S. No | COMPOUND NAME | PLANT SOURCE | REFERENCE |
|---|---|---|---|
| 1 | Pipataline | *Piper brachystachyum* | Phytochemistry, 1988, 27, 3523. |
|  |  | *Piper peepuloides* | Planta Medico, 1973, 23, 295. |
|  |  | *Piper sylvaticum* | Phytochemistry, 1990, 29, 2733 |
| 2. | Sesamin | *Piper brachystachyum* | Indian Journal of Chemistry, 1976, 14B, 389. |
|  |  | *Piper guineense* | Journal of the Chemical Society, Perkin transactions I, 1974, 19, 2 195. |
|  |  | *Piper longum* | Indian Journal of Chemistry, 1966, 4, 252. |
|  |  | *Piper lowong* | Phytochemistry, 1993, 33, 523. |
|  |  | *Piper peepuloides* | Planta Medica,\913, 23, 295. |
|  |  | *Piper sylvaticum* | Phytochemistry, 1974, 13, 2327 |
|  |  | *Piper retrofractum* | Phytochemistry, 1 985, 24, 279 |
| 3. | Pellitorine | *Piper attenautunt* | Indian Journal of Chemistry 1979, 17B, 538. |
|  |  | *Anacyclus pyrethrum* | J. Am. Chem. Soc., 1949, 71, 366–7. |
|  |  | *Piper chaba* | Fltoterapia, 1995, 66, 188. |
|  |  | *Piper guineense* | Toxicon, 1992.30, 1037. |
|  |  | *Piper longum, Piper peepuloides* | Indian Journal of Chemistry, 1 967, 5, 588. |
|  |  | *Piper nepalens* | Phytochemistry, 1972, 11, 2646. |
|  |  | *Piper nigrum* | Journal of Agricultural and Food Chemistry, 1981, 29, 115. |
|  |  | *Piper ribesioides* | Plata Medica, 1989, 55, 193. |
|  |  | *Piper sarmentosum* | Tetrahedron, 1987, 43, 3689. |
|  |  | *Piper sylvaticum* | Experientia, 1974, 30, 223. |
|  |  | *Fagara xanthoxylodea* | Journal of Chemical Society, 1963, 3503–5. |
| 4. | Guineensine | *Piper attenauium* | Indian Journal of Chemistry 1979, 17B, 538. |
|  |  | *Piper guineense* | Journal of the Chemical Society, Perkin transactions I, 1974, 19, 2195. |
|  |  | *Piper brachys tachyum* | Phytochemistry, 1988, 27, 3523. |
|  |  | *Piper longum* | Chem. pharma. BulL, 1983, 31, 3562. |
|  |  | *p. nigrum* | Chem. pharma. BulL, 1988, 36, 2452 |
|  |  | *Piper officinarum* | Phytochemistry, 1976, 15, 425. |
|  |  | *Piper sylvaticum* | Indian Journal of Chemistry 1980, 19B, 346. |
| 5. | Brachyslamide-B | *Piper brachystachyum* | Phytochemistry, 1989, 28, 3039. |
|  |  | *Piper longum* | Nat. Prod. Sci,, 4(1), 23–25, 1999. |

*Piper* compounds show a wide range of biological activities. Biological activities of pipataline, sesamin, pellilorine, guineensine and brachystamide-B are depicted in Table 2.

TABLE 2

| S. No. | COMPOUND NAME | BIOLOGICAL ACTIVITY | REFERENCE |
|---|---|---|---|
| 1. | Pipataline | — | — |
| 2 | Sesamin | Anti oxidant | R-Sac. Chew., 181, 230–5, 19__6 |

TABLE 2-continued

| S. No. | COMPOUND NAME | BIOLOGICAL ACTIVITY | REFERENCE |
|---|---|---|---|
| | | Anti fungal | J. Chem. Ecol., 22(7), 1325–1330, 1998. |
| | | Anti bacterial | Fitoterapia __, 89–92, 1999. |
| | | Live protective, antioxidant | Food Style., 21, 2(12), 35–38. |
| | | Anti feedant | Fitoterapia, 72 (5), 538–543. |
| 3. | Pellitorine | Insecticidal activities against Moth fly (*Telmatoscopus Albipunctatus*). | Pestc. sci. 1991, 18(3), 211–21. |
| | | Insecticidal against *Musca Domestica* | Toxicon, 1992.30, 1037. |
| | | Insectgrowth inhibitor against *p. gossipiella*, *H. virescens*, *H. ze* | Experientia 1984, 40(4), 340–1. |
| | | Larvicida activity against *Aedus Eriseratus* larvae. | J. Chem. Ecol. 1980, 6(1), 35–48. |
| | | Antituberculotic against 8 Mycobacterium stains | Bull. Med Ethno Bot. Res. 1980, (1), 99–106. |
| | | Ovicidal against *Leplinotarsa dectmlineata* | Biosci. Biotechnol. Biochem., 1994, 58(5), 936–7 |
| | | Local anaesthetic | Journal of Chemical Society 1963, 3503-5- |
| | | Insecticidal against *Collosobruchus chinenses* | Journal of Agricultural and Food Chemistry, 1981, 29, 1 15. |
| | | Antifungal against *Cladosporiumsphaerosperm* | Phytochemistry, 55(6), 621–626, 2000. |
| 4. | Guineensine | Insectcidal against *Collosobruchus chinenses* | Journal of Agricultural and Food Chemistry, 1981, 29, 1 15. |
| | | Larvicidal against *Toxocara canis* | Chem. Pharma. Bull., 1988, 36, 2452 |
| | | Insecticidal activity | J. Ind. Chem. Soc., 76(1 1–12), 713–717. |
| 5. | Brachystamide-B | | |

OBJECTS OF THE INVENTION

The main object of the invention is to provide a new activity for pipataline or sesamin or pellitorine or guineensine or brachystamide-B obtained from *Piper longum* as α-glucosidase inhibitors.

Another object of the present invention is to provide a method of treating a subject to obtain α-glucosidase inhibition in said subject.

Another object of this invention relates to therapeutic application of these compounds as α-glucosidase inhibitors in the management and treatment of human diseases like hyperglycemia, hyperinsulinemia, hyperlipoproteinemea, cancer, viral infection, hepatitis B and C, HIV and AIDS etc.

Another object of the present invention is to provide a method of treating a subject to achieve α-glucosidase inhibition in the subject using a pharmaceutical composition comprising pipataline or sesamin or pellitorine or guineensine or brachystamide-B obtained from *Piper longum*.

Furthermore, the object of the invention relates to the isolation of pipataline from an entirely new source.

Still another object of the invention relates to the isolation of five compounds, namely pipataline, sesamin, pellitorine, guineensine and brachystamide-B from *P. longum*.

Still another object of the invention is to provide a process for isolating pipataline or sesamin or pellitorine or guineensine or brachystamide-B obtained from *piper longum* in good yields.

SUMMARY OF THE INVENTION

Accordingly, the present invention relates to a method for providing α-glucosidase inhibition to a subject by administering a pharmaceutical composition comprising a α-glucosidase inhibitory agent selected from pipataline (formula 1a), sesamin (formula 1b), pellitorine (Formula 1c), guineensine (Formula 1d) and brachystamide-B (formula 1e).

The present invention relates to a new activity for pipataline or sesamin or pellitorine or guineensine or brachystamide-B obtained from *Piper longum* as an α-glucosidase inhibitor in the management and treatment of human diseases like hyperglycemia, hyperinsulinemia, hyperlipoproteinemea, cancer, viral infection, hepatitis B and C, HIV and AIDS.

The invention also relates to isolation of pipataline from a new source, namely *Piper longum*. Another aspect of the invention is to provide a process for isolating pipataline or sesamin or pellitorine or guineensine or brachystamide-B obtained from *Piper longum* in good yields.

DETAILED DESCRIPTION OF THE INVENTION

In accordance to the objectives of the invention, the present invention provides a method for providing α-glucosidase inhibition to a subject, said method comprising administering to the subject an effective amount of a pharmaceutical composition comprising an α-glucosidase inhibitory agent selected from pipataline (formula 1a), sesamin (formula 1b), pellitorine (Formula 1c), guineensine (Formula 1d) and brachystamide-B (formula 1e) along with a pharmaceutically acceptable ingredient in management and treatment of diseases like hyperglycemia, hyperinsulinemia, hyperlipoproteinemea, cancer, viral infection, hepatitis B and C, HIV and AIDS in the subject.

In an embodiment of the invention, pipataline provides α-glucosidase inhibitory activity up to 77.45% with an $IC_{50}$ value of 26.52 (μg/ml).

In another embodiment of the invention, sesamin provides α-glucosidase inhibitory activity up to 76.18% with an $IC_{50}$ value of 36.35(μg/ml).

In another embodiment of the invention, pellitorine provides α-glucosidase inhibitory activity up to 86.03% with an $IC_{50}$ value of 34.43(μg/ml).

In another embodiment of the invention, guineensine provides α-glucosidase inhibitory activity up to 61.71% with an $IC_{50}$ value of 20.15(μg/ml).

In another embodiment of the invention, brachystamide-B provides α-glucosidase inhibitory activity up to 73.90% with an $IC_{50}$ value of 33.61(μg/ml).

In another embodiment of the invention, the pharmaceutical composition containing pipataline or sesamin or pellitorine or guineensine or brachystamide-B optionally consists of pharmaceutically acceptable ingredients.

Still another embodiment of the present invention provides a process for isolation of pipataline from *Piper longum* for the first time.

One more embodiment of the invention provides a process of isolation of an α-glucosidase inhibitory agent selected from pipataline (formula 1a), sesamin (formula 1b), pellitorine (Formula 1c), guineensine (Formula 1d) and brachystamide-B (formula 1e) from the plant source *Piper longum*, the process comprising the steps of:

a. extraction the dried fruits of *Piper longum* with a solvent,
b. concentrating the extract under vacuum to obtain a residue;
c. eluting the residue of step (b) with hexane to obtain pipataline and a residue,
d. eluting the residue of step (c) with about 3% ethyl acetate in hexane to obtain sesamin and a residue,
e. eluting the residue of step(d) with about 5% ethyl acetate in hexane to obtain pellitorine and a residue,
f. eluting the residue of step(e) with about 10% ethyl acetate in hexane to obtain guineensine and a residue; and
g. subjecting further elution of the residue of step (f) with about 11% ethyl acetate in hexane to obtainbrachystamide-B.

In one embodiment, the solvent used in step (a) is selected from hexane, cyclohexane or n-pentane.

Another embodiment of the invention relates to the isolation of pipataline from an entirely new source.

Still another embodiment of the invention relates to the isolation of these compounds from *Piper longum* as α-glucosidase inhibitors.

The present invention embodies the isolation of pipataline, sesamin, pellitorine, guineensine, brachystamide-B as α-glucosidase inhibitory principles from *Piper longum* among which pipataline is from an entirely new source.

The present invention relates to the isolation of five compounds, namely pipataline [5-(1-dodecenyl)-1,3-benzodioxol], sesamin [5,5-(tetrahydro-1H,3H-furo {3,4-e)furan-1,4-diyl] bis-1,3-benzodioxol], pellitorine [N-(2-methyl propyl)-2,4-decadienamide], guineensine [13-(1,3-benzodioxol-5-yl)-N {2-methyl propyl)-2,4,12-tridecatrienamide], brachystamide-B [[15-(1,3-benzodioxol-5-yl)-N(2-methyl propyl)-2,4,14-pentadecatrienamide] from the plant source *Piper longum* in significant yields. Among the above said compounds pipataline is from an entirely new source. This invention also relates to the new use of these compounds as α-glucosidase inhibitors.

The present invention embodies isolation of of pipataline, sesamin, pellitorine, guineensine and brachystamide-B, five α-glucosidase inhibitory principles from *Piper longum*, among which pipataline is from an entirely new source.

BRIEF DESCRIPTION OF THE DRAWINGS

The invention is illustrated by the accompanying drawings wherein:

FIG. 1(a) represents the formula of pipataline [5-(1-dodeeenyl)-1,3-benzodioxol];

FIG. 1(b) represents the formula of sesamin [5,5-(tetrahydro-1H, 3H-furo(3,4-e) furan-1,4-diyl) bis-1,3-benzodioxol];

FIG. 1(c) represents the formula of pellitorine (N-(2-methyl propyl)-2,4decadienamide];

FIG. 1(d) represents the formula of guineensine [1,3-(1,3-enzodioxol-5-yl)-N (2-methyl propyl)-2,4,12-tridecatrienamide);

FIG. 1 (e) represents the formula of brachystamide-B [[1,5-(1,3-benzodioxol-5-yl)-N (2-methyl propyl)-2,4,14-pentadecatrienamide;

Figure 2:
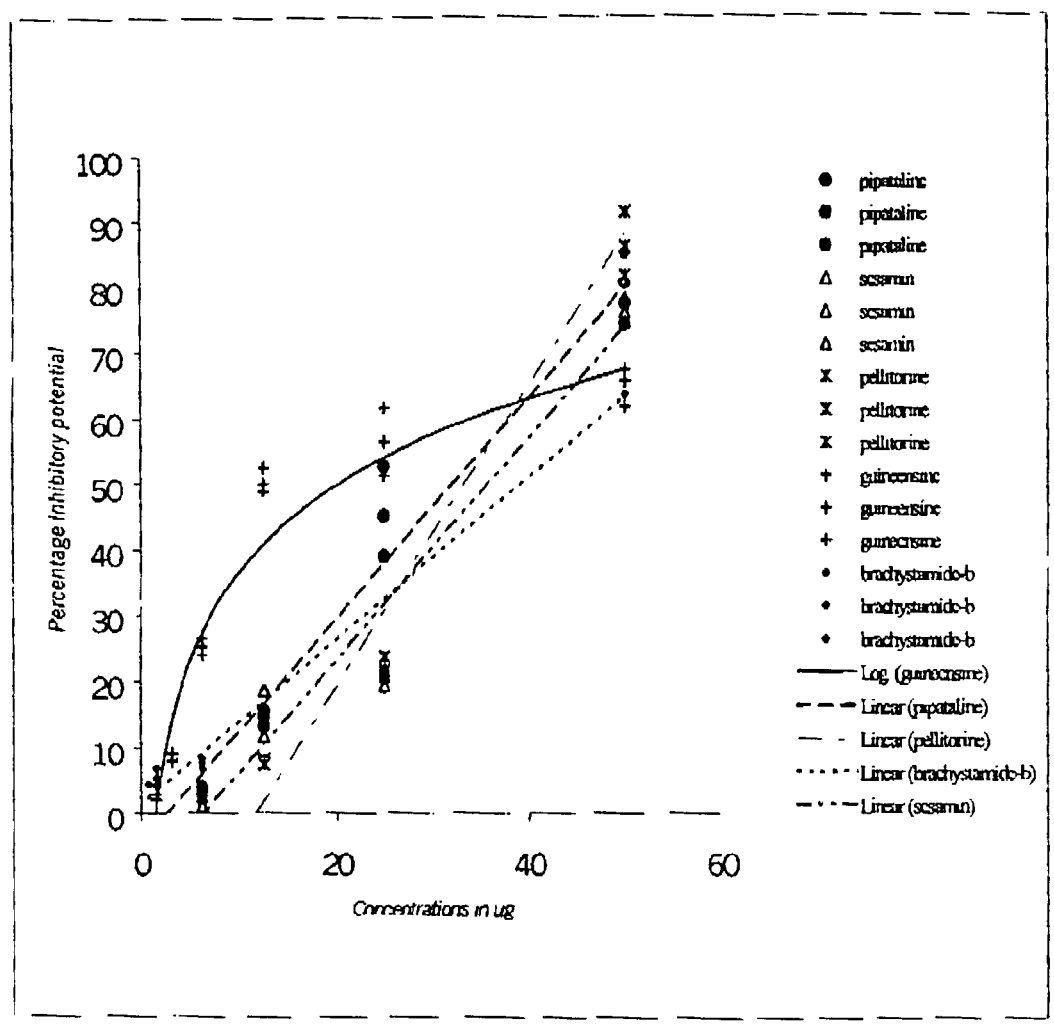
FIG. 2(a) is a graphical representation depicting the α-glucosidase inhibitory activity of pipataline, sesamin, pellitorine, guineensine and brachystamide-B.

Some of the embodiments of the present invention are represented by the following examples, which should not be construed as limitations on the inventive scope of this invention.

In another embodiment of the invention, pipataline obtained from *piper longum* has the following spectrochemical and physical properties.

Molecular Formula: $C_{19}H_{28}O_2$
MP: 38° C.
IR (KBr) $\gamma_{max}$ cm$^{-1}$
2829,1468,1248,1040,980,960.
$^1$H NMR (200 MHz, CDCl$_3$)(δ)
0.95 (3H, t, H-1), 1.20–1.60 (16H, b, H-2-9), 2.20 (2H, q, H-10), 5. 90(2H, s, —OCH$_2$O), 6.0–6.15 (1H, q, H-1 1), 6.30 (1H, d, J=15.5 Hz, H-12), 6.70 (2H, s, H-5', 6'), 6.88 (1H, s, H-2$^1$).
$^{13}$C NMR (50 MHz, CDCl$_3$)
14.12 (C-1), 22.71 (C-2), 29.37–29.66 (C-3-8), 31.95 (C-9), 32.95 (C-10), 100.89 (—), 105.46 (C-20, 108.20 (C-5$^1$), 120.17 (C-6'), 129.27 (C-11), 129.57 (C-1 2), 132.61 (C-1'), 146.68 (C-4'), 148.01 (C-3')
EI-MS
M$^+$288

In another embodiment of the invention, sesamin has the following spectrochemical and physical properties:
Molecular Formula: $C_{20}H_{18}O_6$
MP: 122° C.
UV $\lambda_{max}$ (EtOH)
286, 235 nm
IR (KBr) $\gamma_{max}$ cm$^{-1}$
2800, 1600, 1071, 925, 913, 718 cm$^{-1}$
$^1$H NMR (200 MHz, CDCl$_3$) (δ):
3.08 (IH, m, H-8), 3.90 (IH, dd, J=10 Hz, 4 Hz, H-2b), 4.20–4.30 (IH, m, H-2a), 4.75 (IH, d, J=5 Hz, H-4), 6.0 (2H, s, —OCH$_2$O—), 6.80 (2H, s, H-2', 5% 6.84 (IH, s, H-6')
EI-MS
$^-$M$^+$354, 203, 161, 149. [α]$_D$+78.30°

In another embodiment of the invention, pellitorine has the following spectrochemical and physical properties:

Molecular formula: $C_{14}H_{25}NO$
MP: 83° C.
UV λmax (EtOH)
260 nm.
IR(KBr) $\gamma_{max}$ cm$^{-1}$
3260, 1655, 1600, 1255 cm$^{-1}$.
H NMR (200 MHz, CDCl$_3$) (δ)
0.91 (6H, d, J=6 Hz), 0.8–1.0 (3H), 1.25 (6H, bs), 1.7–2.4 (3H, m), 3.15 (2H, t), 5.55 (IH, t), 5.75 (IH, d, J=15 Hz), 6.0–6.2 (2H, m), 6.80–7.20 (IH, m).
EI-MS m/z (%)
223 (M$^+$, 33), 208 (7), 180 (6), 166 (6), 152 (33), 151 (100), 96 (50), 81 (64), 72 (4), 57 (16), 43 (10).

In another embodiment of the invention, guineensine [13-(1,3-benzodioxol-5-yl)-N(2-methyl propyl)-2,4,12-tridecatrienamide) has the following spectrochemical and physical properties:

Molecular Formula: $C_{24}H_{33}NO_3$
MP: 119° C.
UV λmax (MeOH)
261 nm.
IR(KBr) Ymax cm$^{-1}$ 3300, 1655, 1630, 1545, 1250, 1035 cm$^{-1}$
'H NMR (200 MHz, CDCl$_3$) (δ)
0.93 (6H, d, J=6.5 Hz), 1.25–1.50 (8H), 1.80 (IH, m), 2.12–2.21 (4H, m), 3.16 (2H, t, J=6.4 Hz), 5.48 (IH, br), 5.74 (IH, d, J=15.0 Hz), 5.93 (2H, s), 6.05–6.15 (3H, m), 6.28 (IH, d, 15.5 Hz), 6.72–6.90 (3H), 7.19 (IH, dd, J=15 Hz, 10Hz).
EI-MS 383 (M$^+$, 35), 249 (32), 180 (22), 152 (45), 135 (100).

In another embodiment of the invention, brachystamide-B has the following spectrochemical and physical properties.

Molecular formula: $C_{26}H_{37}NO_3$
UV λmax (EtOH)
260, 208 nm.
IR (KBr) $y_{max}$
1654, 1625, 1000.
'H NMR (200 MHz, CDCl$_3$) (δ)
0.86 (6H, d, H-3", 4"), 1.20–1.70 (12H, b, H-7–12), 1.70–1.90 (IH, m, H-2'), 2.05–2.20 (2H, m, H-6, 15), 3.15 (2H, t, H-1"), 5.68 (IH, d, J=15.5 Hz, H-2), 5.84 (2H, s, —OCH$_2$O—), 5.95–6.15 (3H, m, H-4, 5, 14), 6.23 (IH, d, J=16 Hz, H-15), 6.72 (2H, s, H-5', 6'), 6.83 (IH, s, H-2\7.12 (IH, m, H-3).
$^{13}$C NMR (50 MHz, CDCl$_3$) (6) 166.39 (C-1), 121.85 (C-2), 142.92 (C-3), 128.33 (C-4), 141.23 (C-5), 32.86 (C-6), 28.64–29.51 (C-7–12), 32.81 (C-13), 129.36 (C-14), 129.42 (C-15), 132.58 (C-1$^1$), 105.48 (C-2'), 147.96 (C-3% 146.59 (C-40, 108.21 (C-5% 120.18 (C-60, 46.97 (C-1"), 28.66 (C-2"), 20.69 (C-3", 4"), 100.88 (—OC&O—).
EI-MS
M$^+$411, 396 (42), 299 (20), 149 (28), 97 (30), 69 (88), 57 (100).

EXAMPLE 1

Experimental Protocol: A Process for the Isolation of Pipataline, Sesamin, Pellitorine, Guineensine and Brachystamide-B.

The dried, powdered fruits of *Piper longum* (500 g) were loaded on a soxhlet apparatus. The powder was extracted with hexane. The hexane extract was concentrated under vacuum. The dark green colored residue was loaded on a silica gel column 60–120 mesh, 3.5-cm diameter column loaded to a height of 60 cm.

Initially the column was eluted with hexane to get pipataline. The yield of pipataline is around 6.0 g. Further elution of the column with 3% ethyl acetate in hexane yielded sesamin. The yield of sesamin is around 200 mg.

Further elution of the column with 5% ethyl acetate in hexane yielded pellitorine. The yield of pellitorine is around 200 mg.

Further elution of the column with 10% ethyl acetate in hexane yielded guineensine. The yield of guineensine is around 300 mg.

Further elution of the column with 11% ethyl acetate in hexane yielded Brachystamide-B. The yield of brachystamide-B is around 120 mg.

All the above compounds were obtained in 90% purity.
The spectrochemical and physical properties of the above said compounds are as under:

Pipataline has the following spectrochemical and physical properties:

Molecular Formula: $C_{19}H_{28}O_2$
MP: 38° C.
IR (KBr) $\gamma_{max}$ cm$^{-1}$
2829, 1468, 1248, 1040, 980, 960.
'H NMR (200 MHz, CDCl$_3$) (δ)
0.95 (3H, t, H-1), 1.20–1.60 (16H, b, H-2–9), 2.20 (2H, q, H-10), 5.90(2H, s, —OCH$_2$O), 6.0–6.15 (1H, q, H-11), 6.30 (1H, d, J=15.5 Hz, H-12), 6.70 (2H, s, H-5', 6'), 6.88 (1H, s, H-2$^1$).
$^{13}$C NMR (50 MHz, CDCl$_3$)
14.12 (C-1), 22.71 (C-2), 29.37–29.66 (C-3–8), 31.95 (C-9), 32.95 (C-10), 100.89 (—), 105.46 (C-20, 108.20 (C-51), 120.17 (C-6$^{\prime}$), 129.27 (C-11), 129.57 (C-1 2), 132.61 (C-1'), 146.68 (C-4'), 148.01 (C-3')
EI-MS
M$^+$288

Sesamin has the following spectrochemical and physical properties:

Molecular Formula: $C_{20}H_{18}O_6$
MP: 122° C.
UV λmax (EtOH)
286, 235 nm
IR (KBr) $\gamma_{max}$ cm$^{-1}$
2800, 1600, 1071, 925, 913, 718 cm$^{-1}$
'H NMR (200 MHz, CDCl$_3$) (δ):
3.08 (IH, m, H-8), 3.90 (IH, dd, J=10 Hz, 4 Hz, H-2b), 4.20–4.30 (IH, m, H-2a), 4.75 (IH, d, J=5 Hz, H-4), 6.0 (2H, s, —OCH$_2$O—), 6.80 (2H, s, H-2', 5% 6.84 (IH, s, H-6')
EI-MS
$^-$M$^+$354, 203, 161, 149. [α]$_D$+78.30°

Pellitorine has the following spectrochemical and physical properties:

Molecular formula: $C_{14}H_{25}NO$
MP: 83° C.
UV λmax (EtOH)
260 nm.
IR(KBr) $\gamma_{max}$ cm$^{-1}$
3260, 1655, 1600, 1255 cm$^{-1}$.
H NMR (200 MHz, CDCl$_3$) (δ)
0.91 (6H, d, J=6 Hz), 0.8–1.0 (3H), 1.25 (6H, bs), 1.7–2.4 (3H, m), 3.15 (2H, t), 5.55 (IH, t), 5.75 (IH, d, J=15 Hz), 6.0–6.2 (2H, m), 6.80–7.20 (IH, m).
EI-MS m/z (%)
223 (M$^+$, 33), 208 (7), 180 (8), 166 (8), 152 (33), 151 (100), 96 (50), 81 (64), 72 (4), 57 (16), 43 (10).

Guineensine [13-(1,3-Benzodioxol-5-yl)-N(2-methyl propyl)-2,4,12-tndecatrienamide) has the following spectrochemical and physical properties:

Molecular Formula: $C_{24}H_{33}NO_3$
MP: 119° C.
UV λmax (MeOH)
261 nm.
IR(KBr) Ymax cm$^{-1}$
3300, 1655, 1630, 1545, 1250, 1035 cm$^{-1}$.
'H NMR (200 MHz, CDCl$_3$) (δ) 0.93 (6H, d, J=6.5 Hz), 1.25–1.50 (8H), 1.80 (IH, m), 2.12–2.21 (4H, m), 3.16 (2H, t, J=6.4 Hz), 5.48 (IH, br), 5.74 (IH, d, J=15.0 Hz), 5.93 (2H, s), 6.05–6.15 (3H, m), 6.28 (IH, d, 15.5 Hz), 6.72–6.90 (3H), 7.19 (IH, dd, J=15 Hz, IOHz).
EI-MS
383 (M$^+$, 35), 249 (32), 180 (22), 152 (45), 135 (100).

Brachystamide-B has the following spectrochemical and physical properties:

Molecular formula: $C_{26}H_{37}NO_3$
UV λmax (EtOH)
260, 208 nm.
IR (KBr) y$_{max}$
1654, 1625, 1000.
'H NMR (200 MHz,CDCl$_3$) (δ) 0.86 (6H, d, H-3", 4"), 1.20–1.70 (12H, b, H-7–12), 1.70–1.90 (IH, m, H-2'), 2.05–2.20 (2H, m, H-6, 15), 3.15 (2H, t, H-1"), 5.68 (IH, d, J=15.5 Hz, H-2), 5.84 (2H, s, —OCH$_2$O—), 5.95–6.15 (3H, m, H-4, 5, 14), 6.23 (IH, d, J=16 Hz, H-15), 6.72 (2H, s, H-5', 6'), 6.83 (IH, s, H-2\7.12 (IH, m, H-3).
$^{13}$C NMR (50 MHz, CDCl$_3$) (6)
166.39 (C-1), 121.85 (C-2), 142.92 (C-3), 128.33 (C-4), 141.23 (C-5), 32.86 (C-6), 28.64–29.51 (C-7–12), 32.81 (C-13), 129.36 (C-14), 129.42 (C-15), 132.58 (C-$^1$), 105.48 (C-2'), 147.96 (C-3% 146.59 (C-40, 108.21 (C-5% 120.18 (C-60, 46.97 (C-1"), 28.66 (C-2"), 20.69 (C-3", 4"), 100.88 (—OC&O—).
EI-MS
M$^+$411, 396 (42), 299 (20), 149 (28), 97 (30), 69 (88), 57 (100).

EXAMPLE 2

Determination of α-Glucosidase Inhibition Activity of Compounds Isolated From *P. longum*:

The α-glucosidase inhibitory assay was done by the chromogenic method. In brief 10 μl of test compounds dissolved in DMSO (5 mg/ml and subsequent dilutions) were incubated for 5 min. with 5 μl of yeast α-glucosidase enzyme prepared in 100 mM phosphate buffer (pH 7.00). After 5 minutes of incubation, 50 ml of 5 mM substrate (p-nitrophenyl-α-D-glucopyranoside prepared in the same buffer) were added. The pre-substrate and 5-min post-substrate addition absorbances were recorded at 405 nm spectrophotometrically. The increases in absorbance from pre-substrate addition to post substrate reaction were obtained. Percent inhibition was calculated by (1-O.D test/O.D control)×100 and inhibitory concentration 50% (IC50) was calculated by applying suitable regression analysis.

In accordance with the practice of this invention, it has been found that pipataline, sesamin, pellitorine, guineensine and brachystamide-B are isolated from *Piper longum* among which pipataline is from an entirely new source. The yields of these compounds are also substantial. Also, it has been found that all the above said compounds show α-glucosidase inhibition property.

ADVANTAGES

α-glucosidase inhibitors recently have attracted attention due to their broad-spectrum activities in disorders of multiple origin viz. diabetes, viral disorders, cancer, HIV, Hepatitis-B and C etc. Much attention being directed now to procure the α-glucosidase inhibitors from natural sources.

The compounds pipataline, sesamin, pellitorine, guineensine, brachystamide-B are used in pure form. Hence, isolation of pipataline, sesamin, pellitorine, guineensine and brachystamide-B from *Piper longum* in significant yields as α-glucosidase inhibitors makes the invention very important.

The invention claimed is:
1. A method for treating a metabolic disease selected from the group consisting of hyperglycemia, hyperinsulinemia and hyperlipoproteinemia in a subject presenting symptoms of the metabolic disease comprising administering to the subject an amount of a compound selected from the group consisting of pipataline

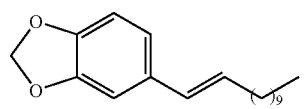

guineensine

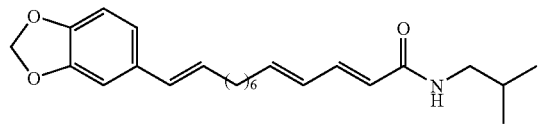

and brachystamide-B

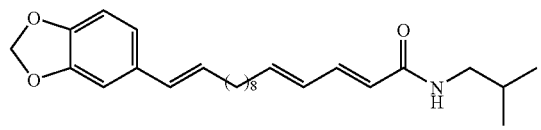

effective for treating the metabolic disease.
2. The method of claim 1, in which the amount of the compound administered is effective to inhibit at least 16.7% of α-glucosidase activity of the subject.

* * * * *